(12) United States Patent
Asao

(10) Patent No.: US 10,179,248 B2
(45) Date of Patent: Jan. 15, 2019

(54) IMPLANTABLE SPACER

(71) Applicant: National University Corporation Gunma University, Gunma (JP)

(72) Inventor: Takayuki Asao, Gunma (JP)

(73) Assignee: National University Corporation Gunma University, Gunma (JP)

( * ) Notice: Subject to any disclaimer, the term of this patent is extended or adjusted under 35 U.S.C. 154(b) by 150 days.

(21) Appl. No.: 15/108,352

(22) PCT Filed: Dec. 25, 2014

(86) PCT No.: PCT/JP2014/084410
§ 371 (c)(1),
(2) Date: Jun. 27, 2016

(87) PCT Pub. No.: WO2015/099089
PCT Pub. Date: Jul. 2, 2015

(65) Prior Publication Data
US 2016/0339265 A1 Nov. 24, 2016

(30) Foreign Application Priority Data
Dec. 27, 2013 (JP) .................................. 2013-271055

(51) Int. Cl.
*A61N 5/10* (2006.01)
(52) U.S. Cl.
CPC ........ *A61N 5/10* (2013.01); *A61N 2005/1087* (2013.01); *A61N 2005/1094* (2013.01); *A61N 2005/1096* (2013.01)

(58) Field of Classification Search
CPC ...... A61F 2210/0076; A61F 2220/0075; A61F 2230/0019; A61N 2005/1094; A61N 2005/1096
See application file for complete search history.

(56) References Cited

U.S. PATENT DOCUMENTS

| | | | |
|---|---|---|---|
| 5,045,708 A | 9/1991 | Cooper | |
| 2007/0191939 A1* | 8/2007 | Ryan | ..................... A61F 2/2448 623/2.36 |

(Continued)

FOREIGN PATENT DOCUMENTS

| | | |
|---|---|---|
| EP | 2497534 A1 | 9/2012 |
| JP | 11-253564 | 9/1999 |

(Continued)

OTHER PUBLICATIONS

Extended European Search Report in EP Application No. 14875858.4 dated Aug. 18, 2017, 6 pages.

(Continued)

*Primary Examiner* — Christine H Matthews
(74) *Attorney, Agent, or Firm* — Marshall, Gerstein & Borun LLP

(57) ABSTRACT

Provided is an implantable spacer that can be placed in a body and can be easily removed after placement. The implantable spacer includes a tube which is folded or bent at one or a plurality of positions to form partial sections adjacent to each other; fixing threads which are disposed along a direction transverse to the partial sections in order to maintain the shape of the tube; and a trigger thread for catching the fixing threads being in a releasable state.

7 Claims, 17 Drawing Sheets

(56) References Cited

U.S. PATENT DOCUMENTS

| | | |
|---|---|---|
| 2007/0239284 A1 | 10/2007 | Skerven et al. |
| 2011/0172697 A1 | 7/2011 | Jönsson |
| 2012/0271093 A1 | 10/2012 | Fukumoto et al. |
| 2013/0006097 A1 | 1/2013 | Mick et al. |
| 2013/0023717 A1 | 1/2013 | Mick et al. |
| 2015/0018764 A1 | 1/2015 | Park et al. |

FOREIGN PATENT DOCUMENTS

| | | |
|---|---|---|
| JP | 2009-521277 A | 6/2009 |
| JP | 2012-502679 A | 2/2012 |
| WO | WO-2005/069309 A1 | 7/2005 |
| WO | WO-2007/040998 A1 | 4/2007 |
| WO | WO-2011/055670 A1 | 5/2011 |
| WO | WO-2013/006556 A2 | 1/2013 |
| WO | WO-2013/122349 A1 | 8/2013 |

OTHER PUBLICATIONS

Search Report in International Application No. PCT/JP2014/084410 dated Apr. 7, 2015.

International Preliminary Report on Patentability and Written Opinion in International Application No. PCT/JP2014/084410 dated Jun. 28, 2016, 6 pages.

Communication in EP Application No. 14875858.4 dated May 3, 2018, 7 pages.

Notification of Reasons for Refusal in JP Application No. 2015-555026 dated Aug. 14, 2018, 4 pages.

\* cited by examiner

IMPLANTABLE SPACER

TECHNICAL FIELD

The present invention relates to an implantable spacer.

BACKGROUND ART

One of available methods for treating diseases such as malignant tumors is particle beam radiation therapy. Particle beam radiation therapy is a method for treating diseases by irradiating a malignant tumor or the like with particle beams, such as heavy particles, to kill cells in the malignant tumor or the like. Particle beam radiation therapy may cause damage to normal organs and the like around a malignant tumor or the like, because normal organs and the like around the malignant tumor or the like are also irradiated with the particle beams.

In particle beam radiation therapy, particle beams irradiated to a tumor can damage any gastrointestinal tract being present at a position in contact with the tumor, resulting in gastrointestinal perforation; and thus some arrangement is needed to avoid concentration of the particle beam radiation dose on the gastrointestinal tract by creating a space between the tumor and the gastrointestinal tract (intestinal tract). To reduce damage to gastrointestinal tracts caused by particle beams, a spacer is conventionally embedded between a tumor and a normal tissue.

FIG. 1 illustrates an example spacer embedded between a tumor and normal organs or the like in the body. According to the example in FIG. 1, a spacer is embedded between the tumor and the normal organs or the like. In addition, the tumor is irradiated with particle beams from outside the body. The size of the irradiation field, which is the area irradiated with particle beams, is to be greater than the size of the tumor. Embedding a spacer between the tumor and the normal organs or the like reduces irradiation of the normal organs or the like with particle beams, which are irradiated toward the tumor.

PRIOR ART REFERENCES

Patent Documents

Patent Document 1: WO 2011/055670
Patent Document 2: Japanese Unexamined Patent Application Publication No. 11-253564

SUMMARY OF INVENTION

Technical Problem

In general, an artificial material such as Gore-Tex is used as a spacer filling the space created between the tumor and the intestinal tract (gastrointestinal tract). The artificial material created as a spacer is embedded in the body through a laparotomy surgery prior to irradiation of particle beams. Because the artificial material is a foreign material to the body, it needs to be removed out of the body after treatment. A laparotomy surgery is to be performed again in order to remove the artificial material after treatment. Laparotomy surgeries put burdens on the patient, and thus the number of laparotomy surgeries needs to be reduced.

In addition, if the intestinal tract has any injury, an infection may be caused when the gastrointestinal tract, i.e., a normal organ, is detached from the tumor so as to create a space between the tumor and the gastrointestinal tract, a normal organ. Accordingly, when the intestinal tract has an injury, it is difficult to retain an artificial material in the body when the intestinal tract has an infection.

An object of the present invention is to provide an implantable spacer that can be placed in the body and can be easily removed after placement.

Solution to Problem

To solve the above-described problems, the present invention employs the method below.

That is, a first aspect employs an implantable spacer comprising:

a tube which is folded or bent at one or a plurality of positions to form partial sections adjacent to each other;

fixing threads which are disposed along a direction transverse to the partial sections in order to maintain a shape of the tube; and a trigger thread for catching the fixing threads being in a releasable state.

Advantageous Effects of Invention

The present invention makes it possible to provide an implantable spacer that can be placed in the body and can be easily removed after placement.

BRIEF DESCRIPTION OF DRAWINGS

FIG. 1 illustrates an example spacer embedded between a tumor and normal organs or the like.

DESCRIPTION OF EMBODIMENTS

Embodiments of the present invention will now be described with reference to the drawings. Configurations of the embodiments are illustrative examples, and configurations of the disclosure are not limited to specific configurations of the embodiments according to the disclosure.

When configurations of the disclosure are implemented, specific configurations according to the embodiments may be employed as appropriate.

Embodiment (Example Configuration)

Figure 2:
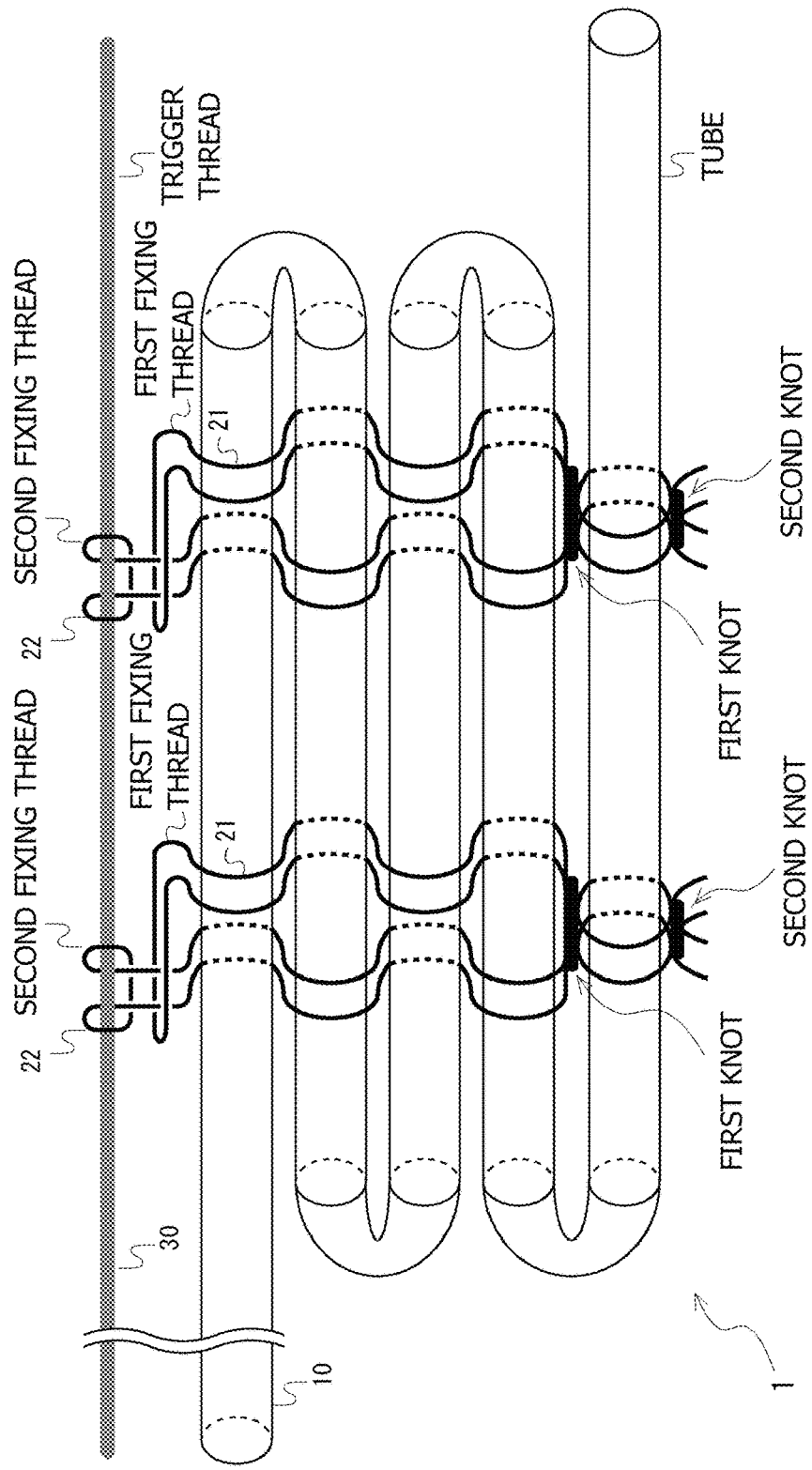
FIG. 2 illustrates an example configuration of the spacer.

FIG. 2 illustrates an example configuration of a spacer according to the present embodiment. The spacer 1 in FIG. 2 includes a tube 10, a first fixing thread 21, a second fixing thread 22, and a trigger thread 30. The pair of one first fixing thread 21 and one second fixing thread 22 may be collectively called fixing threads 20. The example in FIG. 2 illustrates the spacer 1 including two pairs of fixing threads 20; however, the spacer 1 may include two or more pairs of fixing threads 20. The example in FIG. 2 illustrates the spacer 1 including one trigger thread; however, the spacer 1 may include a plurality of trigger threads 30. Dotted lines in the first fixing thread 21 or the second fixing thread 22 in FIG. 2 represent that the first fixing thread 21 or the second fixing thread 22 in the dotted portion passes on the back side of the tube 10.

The tube 10 has elasticity and is folded a plurality of times. Folding the tube 10 a plurality of times causes folded portions of the tube 10 to come closer to each other or come together to form a wavy structure. A partial section formed by folding the tube 10 is hereinafter simply called a partial section. The wavy structure excluding both end portions of the tube 10 is hereinafter called the planar portion of the tube 10. The wavy structure can also be described as raft-like. Note that the tube 10 may be folded at least once to form adjacent partial sections. The tube 10 may also be bent at one or more positions to form adjacent partial sections. In addition, the tube 10 may include both of a folding area and a bending area. The fixing threads 20 bind the tube 10 into the shape of the planar portion by running in the planar portion of the tube 10 along the outer surface of the tube 10 in a direction transverse to the tube 10, in such a way as to weave adjacent partial sections of the folded tube 10 between the near side (front side) seen from one face of the planar portion and the back side in an alternate manner. The first fixing thread 21 and the second fixing thread 22 are passed through the planar portion so that, on partial sections, one of the threads contacts one side of the outer surface of the tube 10 while the other thread contacts the opposite side thereof. Each of the first fixing thread 21 and the second fixing thread 22 is folded at one end, forming a loop at the folding area, and passes through the planar portion in a pair of threads starting from the loop, i.e., in the form of a double line. The loop at the tip of the second fixing thread 21 is passed through the loop at the tip of the first fixing thread 22 at a further outward position from the partial section of the tube 10 located at one end of the planar portion, with the result that the tip of the first fixing thread 21 is caught by the second fixing thread 22. On the other hand, the tip of the second fixing thread 22 is caught by the trigger thread 30 at a position further extended from the partial section of the tube 10 at one end of the planar portion.

That is, the trigger thread 30 is passed through the loop of the second fixing thread 22 at its tip extended from one end of the planar portion. No limitation is imposed on how the trigger thread 30 and the second fixing thread 22 are caught by each other. For example, the loop at the tip of the second fixing thread 22, being a pair of threads of the second fixing thread 22, may be further folded to create a loop for each of the pair of threads so that the trigger thread 30 is passed through the individual loops. The trigger thread 30 and the second fixing thread 22 are caught by each other in such configuration, which allows them to be uncaught by pulling out the trigger thread 30. When the trigger thread 30 is pulled out to be off the second fixing thread 22, which in turn allows the first fixing thread 21 and the second fixing thread 22 to be uncaught. For example, pulling out the trigger thread 30 causes the first fixing thread 21 and the second fixing thread 22 to be uncaught. The fixing threads 20 now being uncaught release the tube 10 that has been bound into the planar shape.

The fixing threads 20 are caught by the trigger thread 30 on one side (hereinafter called a first side) of the planar portion, while a first knot is created by tying the first fixing thread 21 and the second fixing thread 22 together between the partial section of the tube 10 located at the end of the other side (hereinafter called a second side) and the partial section adjacent thereto (the second partial section from the end of the second side). The first side and the second side respectively form a side on either end of the planar portion.

At the first knot, the first fixing thread 21 and the second fixing thread 22 are tied together so as not to release the tube 10 and the trigger thread 30 easily. In addition, the first fixing thread 21 and the second fixing thread 22 are led from the first knot to the outside of the tube 10's partial section located at the end of the second side, and then the first fixing thread 21 and the second fixing thread 22 are tied together to create a second knot. There is no specific limitation on how the threads are tied together at the first and second knots. The first and second knots ensure that the fixing threads 20 are fixed to the tube on the other end of the planar portion. When the trigger thread 30 is pulled out, the first fixing thread 21 and the second fixing thread 22 are released on the trigger thread 30 side starting from the first knot.

The example in FIG. 2 illustrates that there is a separation between the trigger thread 30 and the tube 10 and between sections of the folded tube 10; however, pulling the fixing threads 20 strongly when tying the fixing threads 20 together at the first knot causes the trigger thread 30 and the tube 10 as well as sections of the folded tube 10 to be in close contact with each other. Note that ellipses are drawn in solid and dotted lines midway in the tube 10 for ease of understanding that the tube 10 is substantially circular in cross section, without the intention to indicate that the tube is bonded or otherwise connected at the respective positions. This applies to the other drawings.

Configurations of the spacer 1 illustrated in FIG. 2 are not limited to the example illustrated in FIG. 2 and its components may be omitted, replaced, or added as appropriate.

As the tube 10, a tube consisting of biocompatible silicone materials, similar to drains used for laparotomy surgeries is used. For example, a 19 Fr biocompatible silicone tube is used as the tube 10. The tube 10 is elastic and bendable. Another biocompatible tube may also be used as the tube 10.

As the fixing threads 20, 4-0 nylon threads are used, for example. As the trigger thread 30, 0 nylon threads are used, for example. Nylon threads used as the fixing threads 20 or the trigger thread 30 are those which can be used for living bodies. Other biocompatible threads may be used as the fixing threads 20 or the trigger thread 30.

Configurations of the spacer 1 will now be described in detail with reference to FIGS. 3 to 13.

Figure 3:
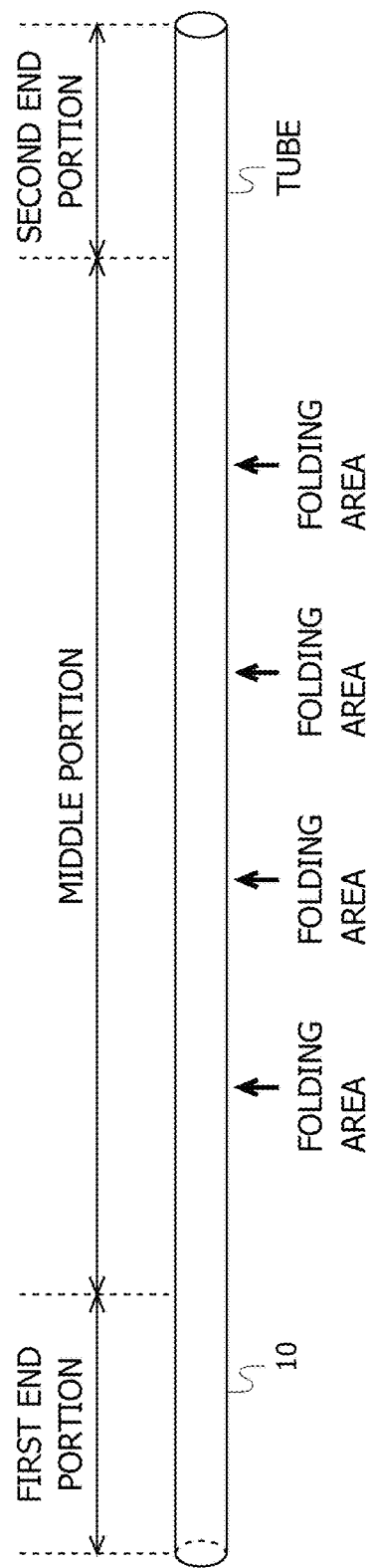
FIG. 3 illustrates an example tube included in the spacer.

FIG. 3 illustrates an example of the tube 10 included in the spacer 1. The tube 10 used for the spacer 1 includes portions called a first end portion, a middle portion, and a second end portion. The first end portion refers to one end portion of the tube 10. The second end portion refers to the other end portion of the tube 10. The middle portion refers to the portion between the first and second end portions. The middle portion includes a plurality of folding areas. The middle portion is folded approximately 180° at a folding area. Part of the first end portion of the tube 10 is led outside the body when the spacer 1 is embedded into the body. Usually, the first end portion is led outside the body by about 30 cm to 40 cm from the end. The middle portion of the tube 10 is folded at a plurality of folding areas. As described with reference to FIG. 2, the middle portion of the tube 10 is fastened with the fixing threads 20. The first end portion, the middle portion, and the second end portion of the tube 10 illustrated in FIG. 3 do not represent actual lengths. The lengths of the first end portion, the middle portion, and the second end portion may be changed as appropriate. The same applies to the tube 10 illustrated in the other drawings.

Figure 4:
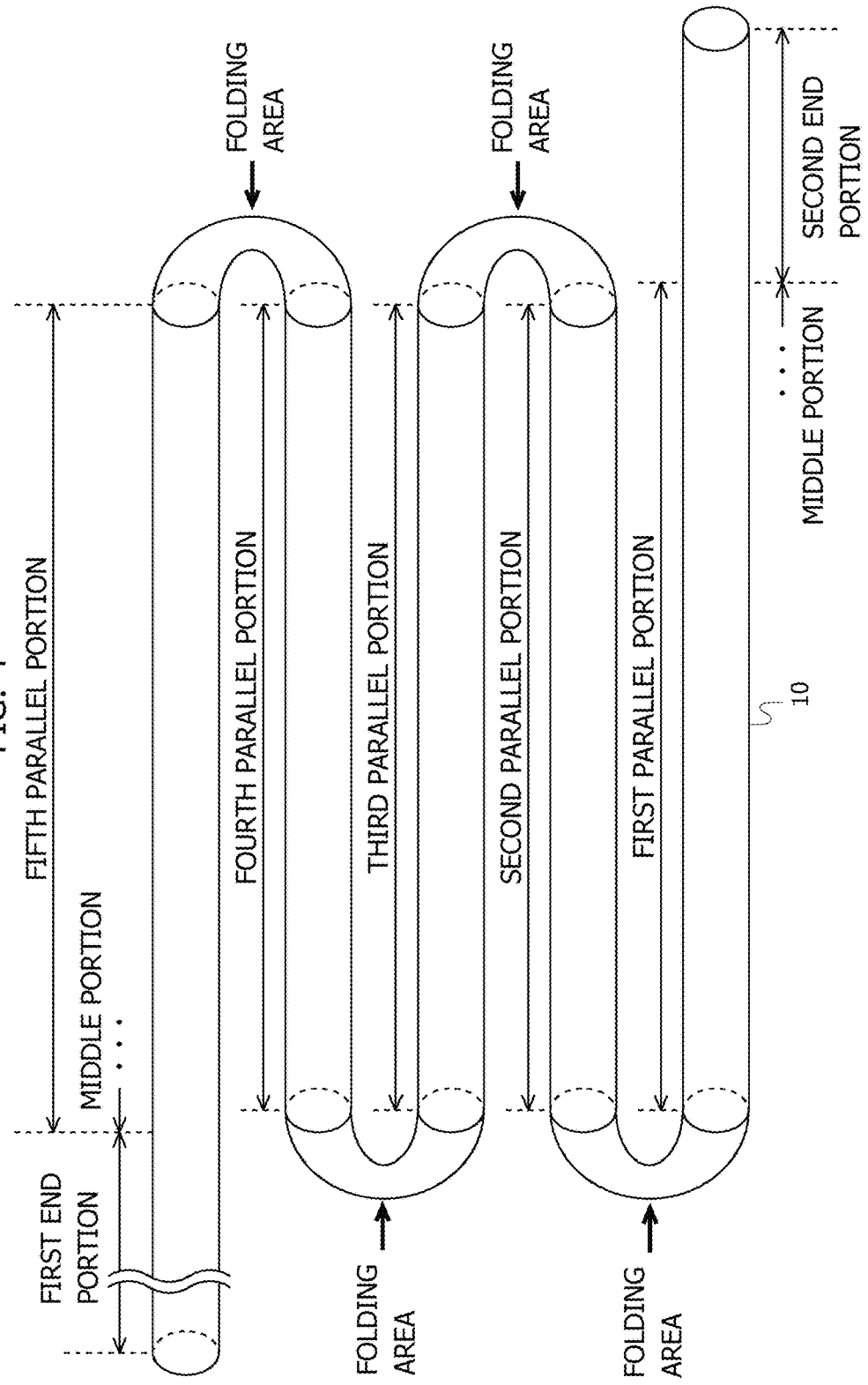
FIG. 4 illustrates an example tube folded at folding areas.

FIG. 4 illustrates an example of the tube 10 folded at folding areas. The tube 10 used for the present embodiment is circular in cross section. The tube circular in cross section means that the shape of a cross section which is seen when the tube is cut along a plane perpendicular to the longitudinal direction of the tube is circular. The example in FIG. 4 illustrates that the tube 10 is folded approximately 180° at each of a plurality of folding areas in the middle portion. The example in FIG. 4 also illustrates that the tube 10 is folded at four areas, and the middle portion of the tube 10 has five partial sections of the tube 10 arranged almost in parallel, forming a wavy structure which is substantially planar with mountains and valleys. In other words, the tube 10 being circular in cross section is folded at a plurality of areas to form a structure shaped like mountains and valleys composed of partial sections adjacent to each other. The five individual partial sections in the middle portion of the tube 10 are called a first parallel portion, a second parallel portion, a third parallel portion, a fourth parallel portion, and a fifth parallel portion, in the order from the closest to furthest to the second end portion. The tube 10 is folded in such a way that air can be passed between the first and second end portions. Air can be passed as above, which makes it possible, when the spacer 1 is embedded in the body, to apply a negative pressure on one end (first end portion side) of the tube 10 coming out of the body, aspirate contaminants in the abdominal cavity (e.g., blood, pus, exudate, or digestive fluid) from the other end of the tube (second end portion side) placed in the body, and bring these contaminants out of the body. Note that the tube 10 according to the present invention is not necessarily circular in cross section. For example, the tube 10 may be triangular, rectangular, pentangular, or otherwise polygonal in cross section. The tube triangular and so on in cross section means that the shape of a cross section which is seen when the tube is cut along a plane perpendicular to the longitudinal direction of the tube is triangular and so on.

Figure 5:
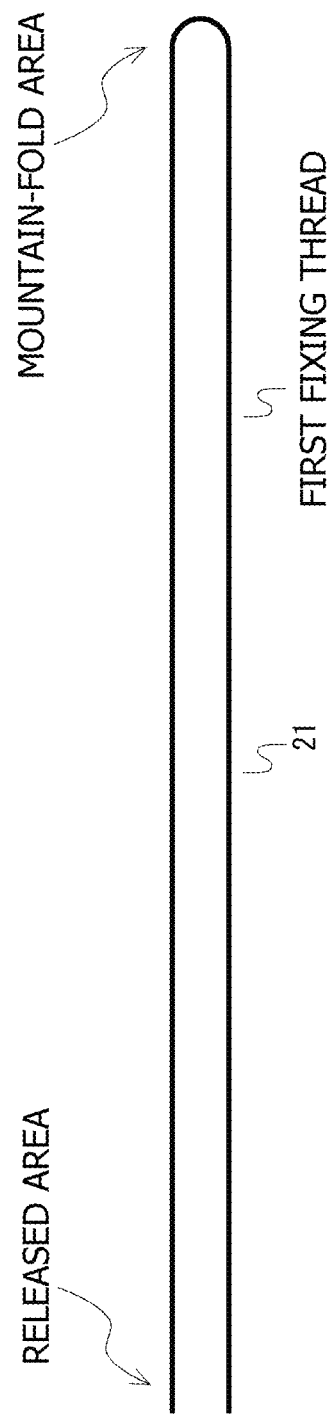
FIG. 5 illustrates an example of a first fixing thread.

FIG. 5 illustrates an example of the first fixing thread. As described with reference to FIG. 2, the first fixing thread 21 is used with its one end being folded; for example, the thread is folded at around the center of the cut thread. The folded area and its opposite area are hereinafter called a mountain-fold area and a released area, respectively, as indicated in FIG. 5. These descriptions of the first fixing thread 21 are also applied to the second fixing thread 22.

Figure 6:
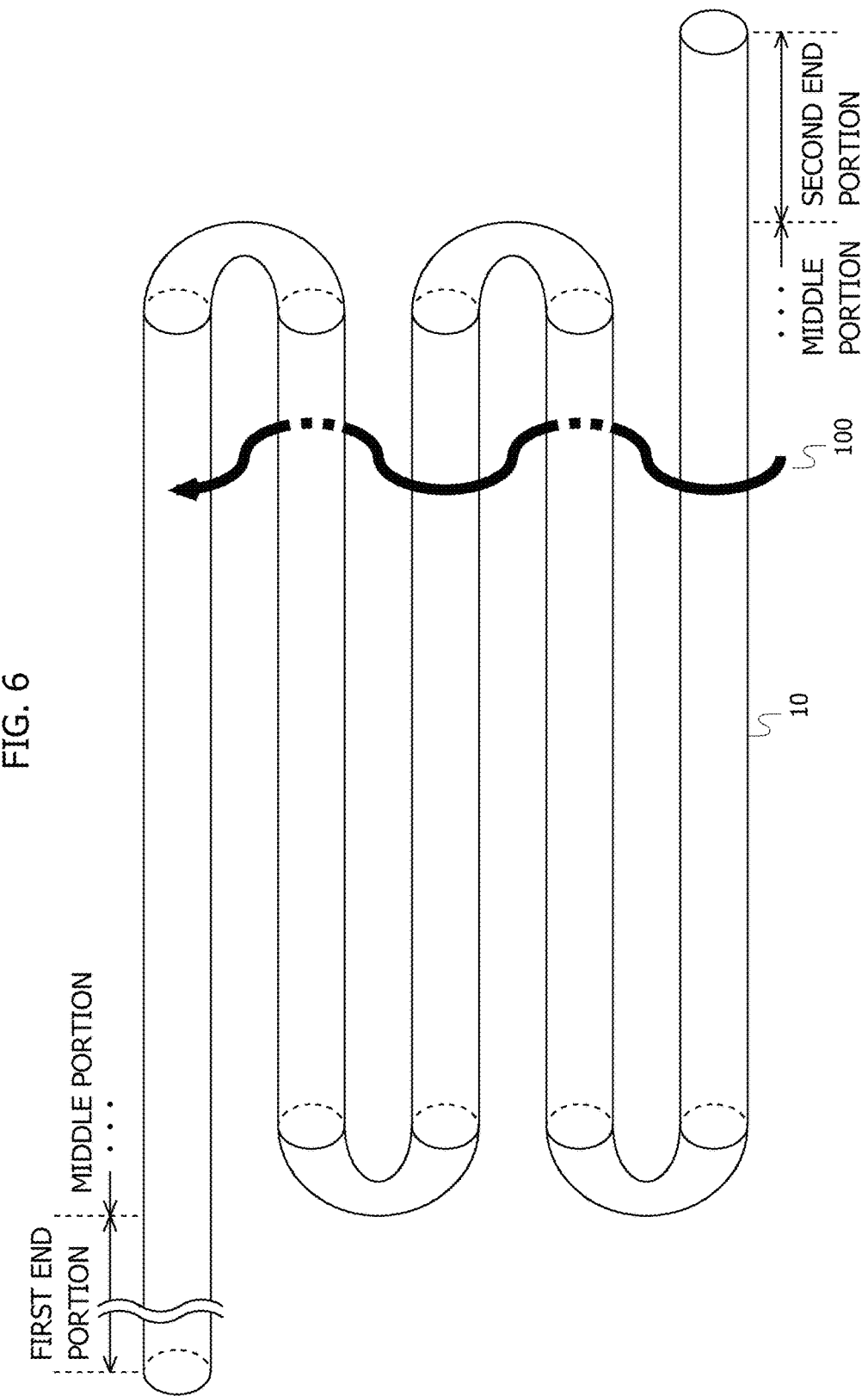
FIG. 6 indicates example positions of the tube on which the first fixing thread is passed.

FIG. 6 indicates example positions of the tube on which the first fixing thread is passed. The first fixing thread 21, with its mountain-fold area placed at the head, runs on the front side of the first parallel portion, on the back side of the second parallel portion, on the front side of the third parallel portion, on the back side of the fourth parallel portion, and on the front side of the fifth parallel portion, as indicated by an arrow 100 in FIG. 6.

Figure 7:
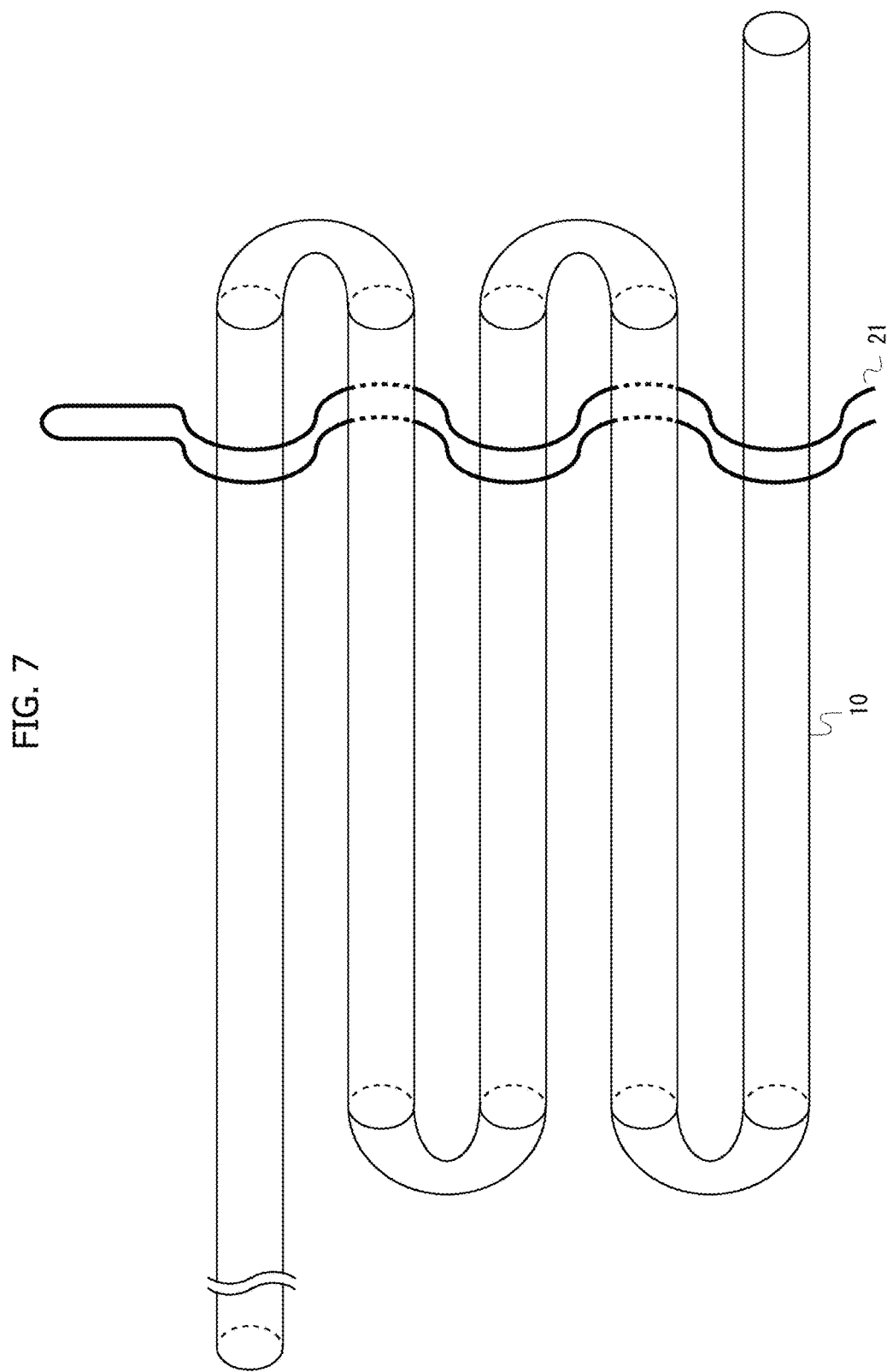
FIG. 7 illustrates an example that the first fixing thread is passed through the middle portion of the tube.

FIG. 7 illustrates an example that the first fixing thread is passed across the middle portion of the tube. As illustrated in FIG. 7, the first fixing thread 21 is passed across the middle portion of the tube 10 by following the arrow 100 in FIG. 6. As seen in FIG. 7, the mountain-fold area of the first fixing thread 21 is on the fifth parallel portion side, while the released area of the first fixing thread 21 is on the first parallel portion side. The first fixing thread 21 is passed across the parallel portions of the tube 10 so as to be almost perpendicular to the longitudinal direction of the tube. In FIG. 7, the parts of the first fixing thread 21 depicted in dotted lines represent that the parts of the first fixing thread 21 are running on the back side of the tube 10. The same applies to the other drawings.

Figure 8:
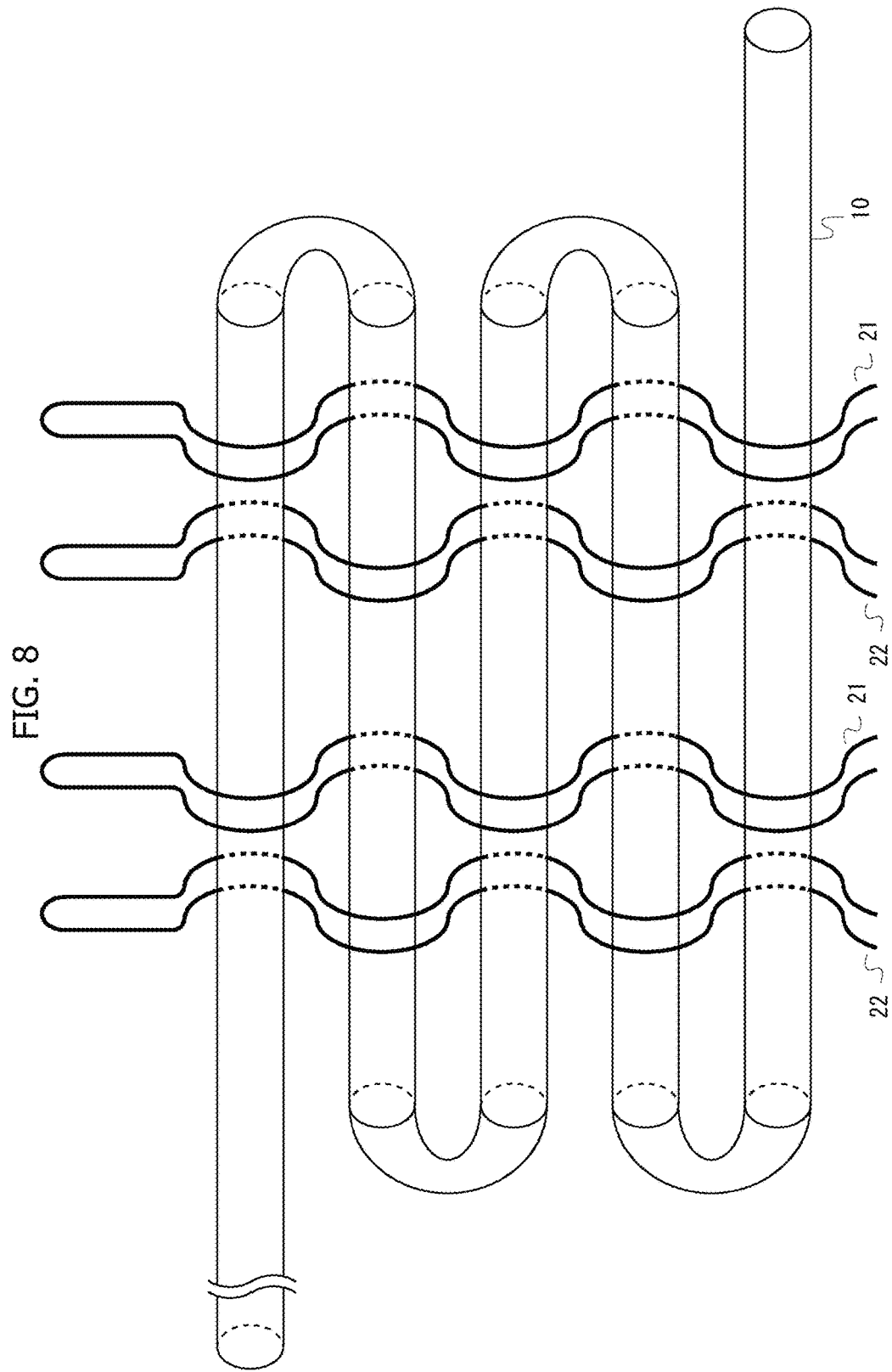
FIG. 8 illustrates an example that two pairs of fixing threads are passed through the middle portion of the tube.

FIG. 8 illustrates an example that two pairs of fixing threads are passed through the middle portion of the tube. The first fixing thread 21 is the same as the example illustrated in FIG. 7. The second fixing thread 22, with its mountain-fold area placed at the head, runs on the back side of the first parallel portion, on the front side of the second parallel portion, on the back side of the third parallel portion, on the front side of the fourth parallel portion, and on the back side of the fifth parallel portion. The second fixing thread 22 is passed through the parallel portions of the tube 10 in an alternate manner with the first fixing thread 21, so as to be almost perpendicular to the longitudinal direction of the tube. The mountain-fold area of the second fixing thread 22 is on the fifth parallel portion side, while the released area of the second fixing thread 22 is on the first parallel portion side. In this way, the fixing threads 20 (the first fixing thread 21 and the second fixing thread 22) are preferably disposed along the structure shaped like mountains and valleys in a direction transverse to the partial sections in order to more securely maintain the shape of the folded tube 10. In other words, the fixing threads 20 are preferably disposed so as to be in close contact with the outer surface of the tube.

Figure 9:
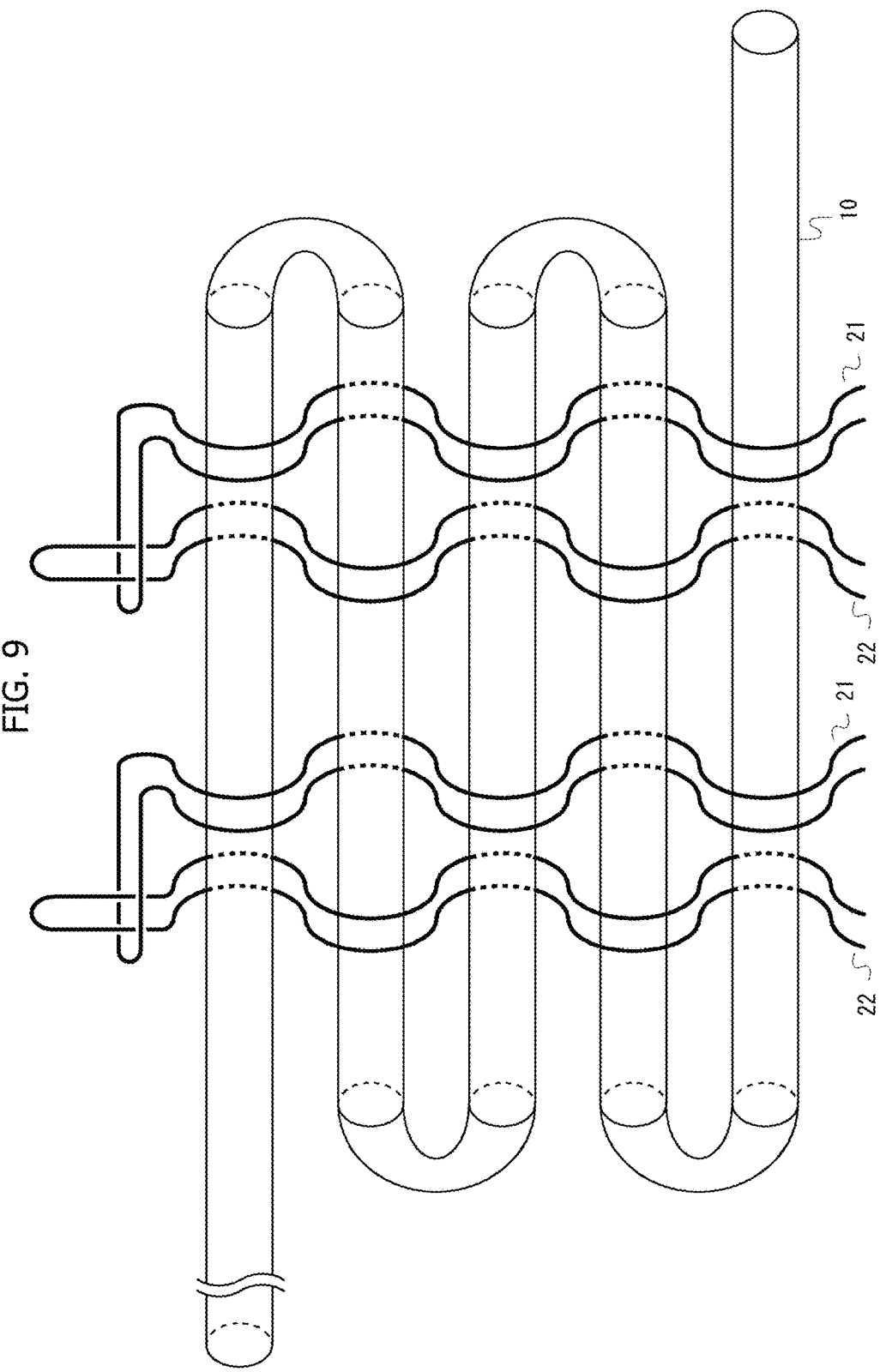
FIG. 9 illustrates an example that a second fixing thread is passed through a first fixing thread.

FIG. 9 illustrates an example that the second fixing thread is passed through the first fixing thread. The mountain-fold area of the second fixing thread 22 is passed inside the mountain-fold area of the first fixing thread 21. Consequently, the first fixing thread 21 becomes caught by the second fixing thread 22.

Figure 10:
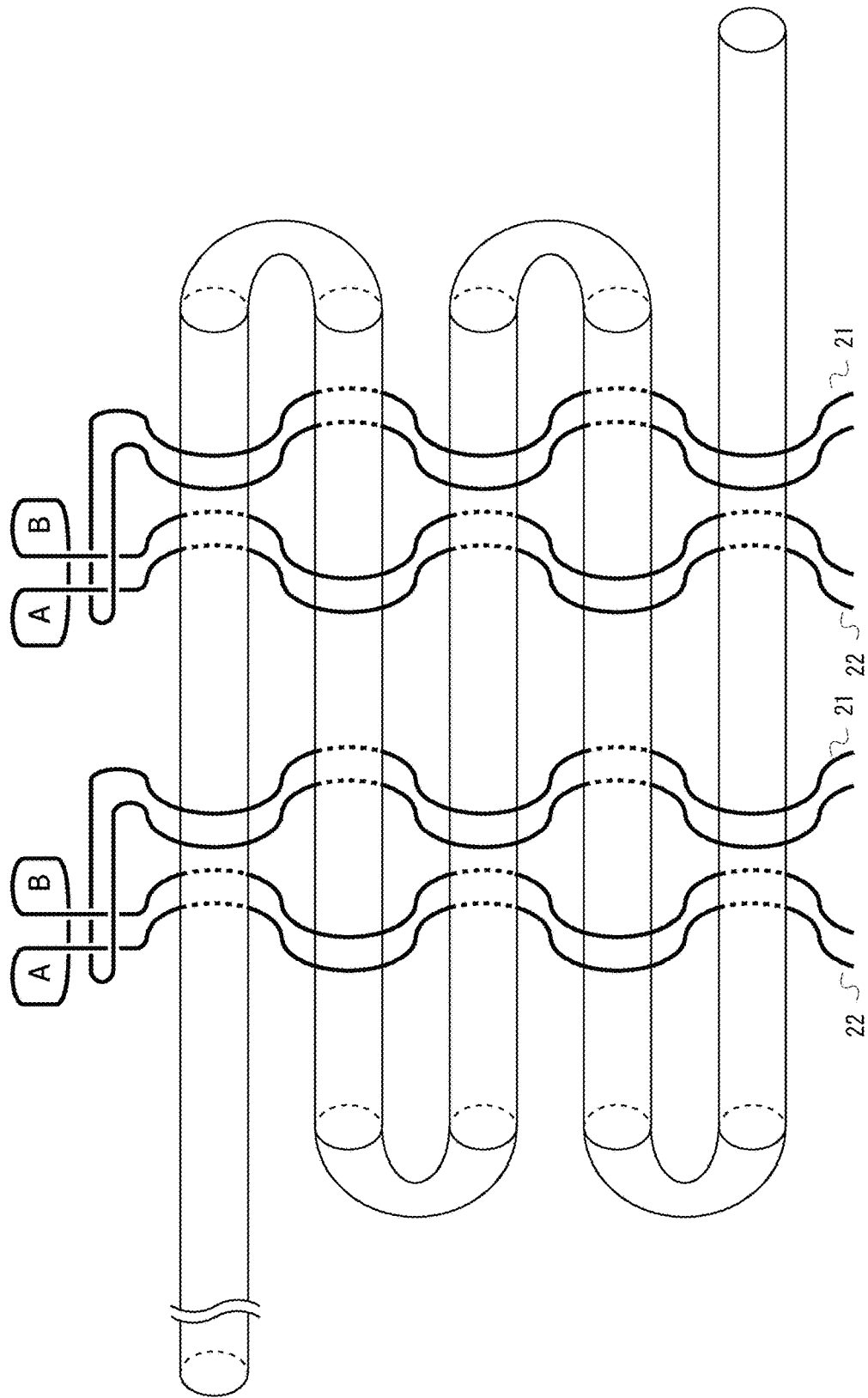
FIG. 10 indicates positions through which a trigger thread is to be passed.

FIG. 10 indicates example positions through which the trigger thread is to be passed. The trigger thread 30 is passed through two rings that are created by folding the mountain-fold area of the second fixing thread 22. According to the example in FIG. 10, the second fixing thread 22 is folded to the back side of the figure to create two rings ("A" and "B" in FIG. 10). Then, the trigger thread 30 is passed through the ring "A" in FIG. 10 from the back side to the front side of the figure and is further passed through the ring "B" from the front side to the back side of the figure. When there are two or more second fixing threads 22, the above procedure is repeated.

Figure 11:
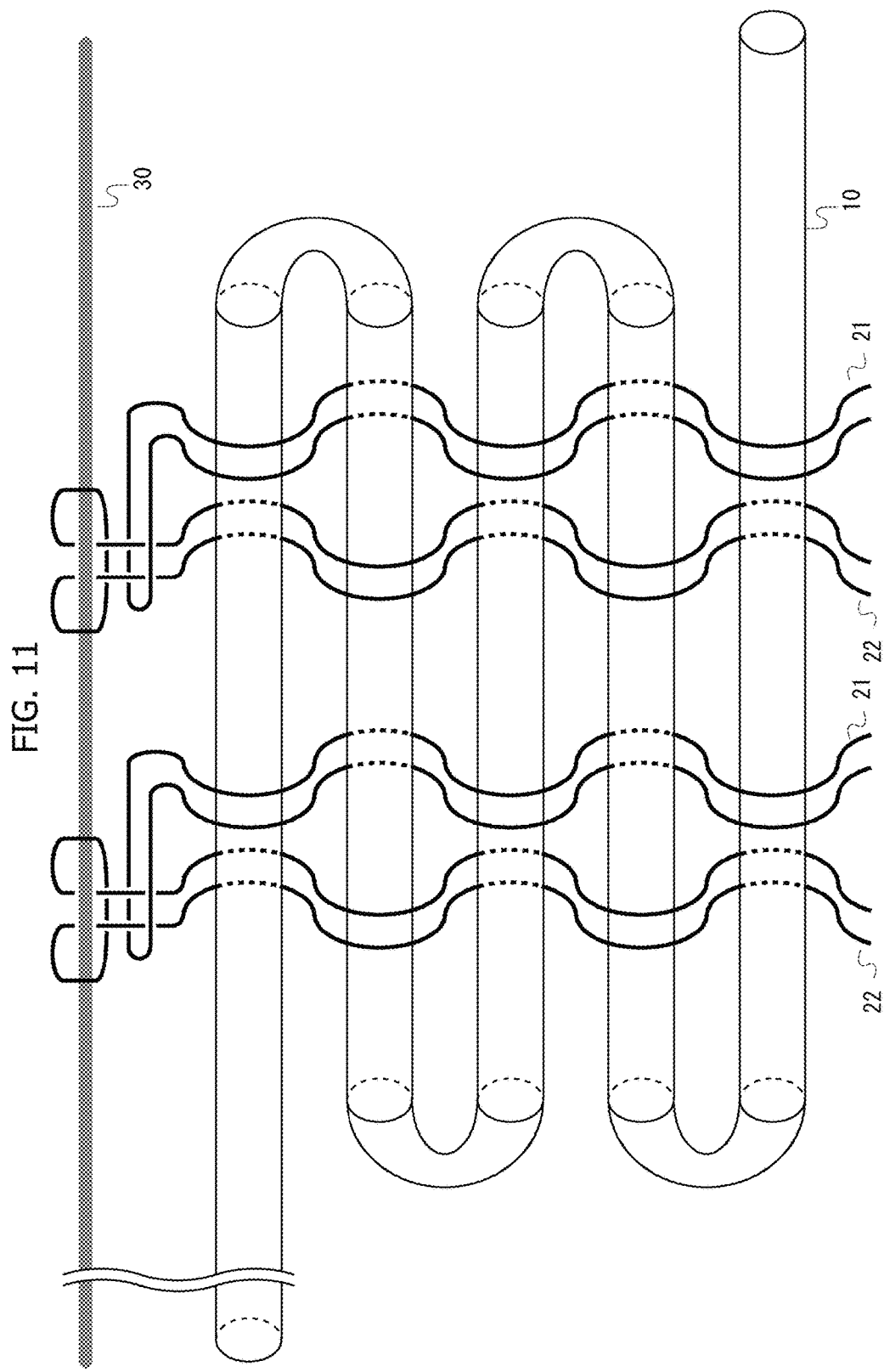
FIG. 11 illustrates an example that the trigger thread is passed through second fixing threads.

FIG. 11 illustrates by an example that the trigger thread is passed through the second fixing threads. Passing the trigger thread 30 through rings of the second fixing thread causes the second fixing thread 22 to be caught by the trigger thread. In addition, pulling out the trigger thread causes the second fixing thread 22 to be released. Furthermore, the first fixing thread 21 is released in conjunction with the release of the second fixing thread 22. How the trigger thread 30 is passed through the second fixing thread 22 is not limited to the method described above. For example, the trigger thread 30 may simply be passed inside the mountain-fold area of the second fixing thread. If the tube 10 in such state is pulled from the first end portion side, the folded portions of the tube are stretched out and the tube 10 recovers its original shape.

Figure 12:
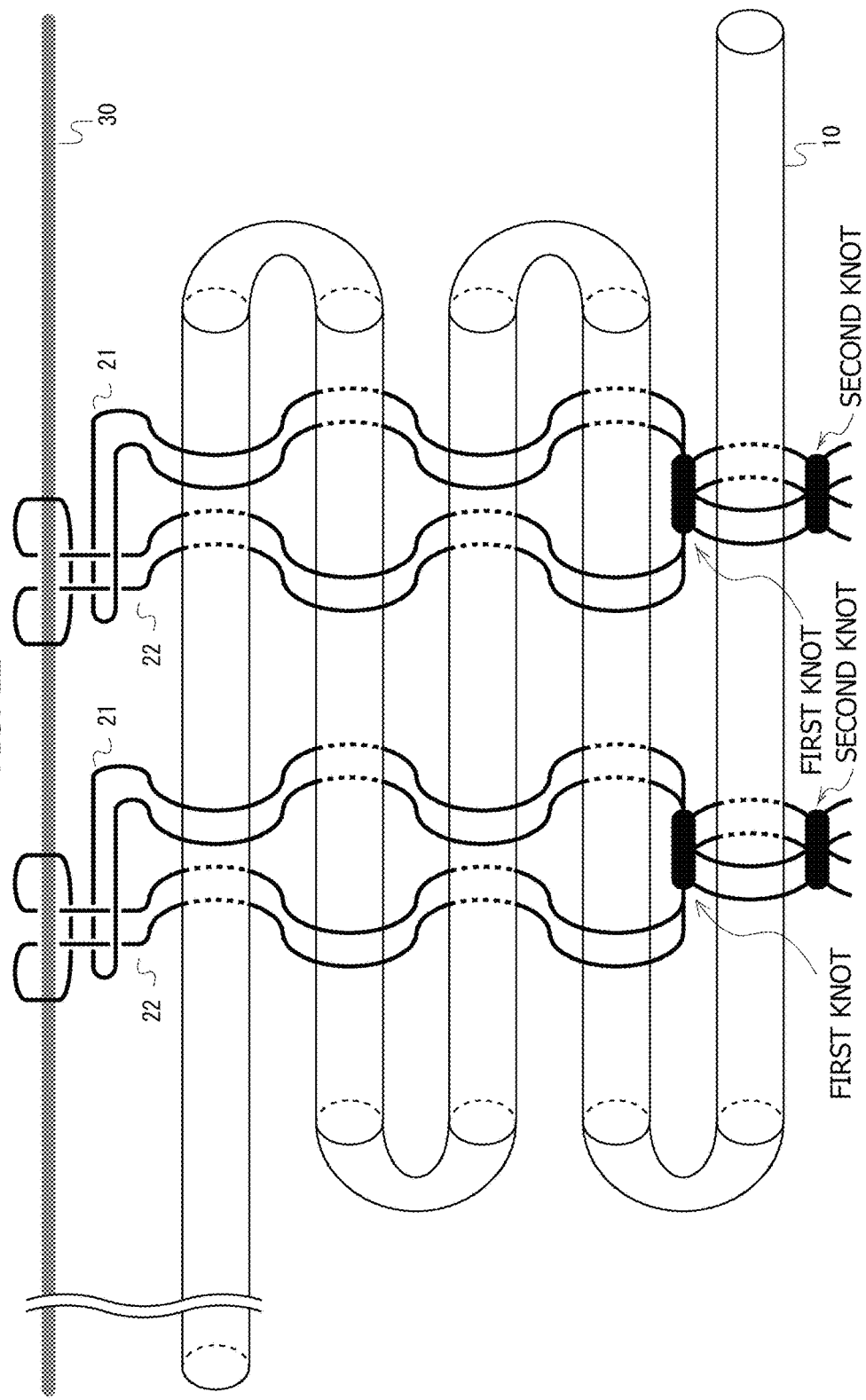
FIG. 12 illustrates examples of a first knot and a second knot.

FIG. 12 illustrates examples of the first and second knots. The first fixing thread 21 and second fixing thread 22 are tied together at two positions around the first parallel portion of the tube 10 to be fixed on the first parallel portion. The two tying positions are hereinafter called a first knot and a second knot. The first knot is present between the first and second parallel portions. The second knot is present on the opposite side of the first parallel portion to the first knot. At the first knot, the first fixing thread 21 and the second fixing thread 22 are tied together so as not to release the trigger thread, the fifth parallel portion, the fourth parallel portion, the third parallel portion, and the second parallel portion easily. No specific limitation is imposed on how the threads are tied together. The example in FIG. 12 illustrates that there is a separation between the trigger thread 30 and the middle portion of the tube 10 and between sections in the middle portion of the tube 10; however, pulling the fixing threads 20 when tying the fixing threads 20 at the first knot causes the trigger thread 30 and the tube 10 as well as adjacent sections of the folded tube 10 to come into close contact with each other. At the second knot, the first fixing thread 21 and the second fixing thread are tied together so that the fixing threads 20 are fixed to the first parallel portion of the tube 10. It should be noted, however, that at the first and second knots the first fixing thread 21 and the second fixing thread are tied together so as not to flatten the tube 10 and eliminate the internal space of the tube 10. Hence, air can be passed between the first and second end portions of the tube 10.

Alternatively, the released areas of the first fixing thread 21 and the second fixing thread 22 may be folded to be brought to the first knot position located between the first and second parallel portions to create a knot at the first knot position, thereby fixing the first fixing thread 21 and the second fixing thread 22 to the first parallel portion of the tube 10 without creating a knot at the second knot position.

Figure 13:
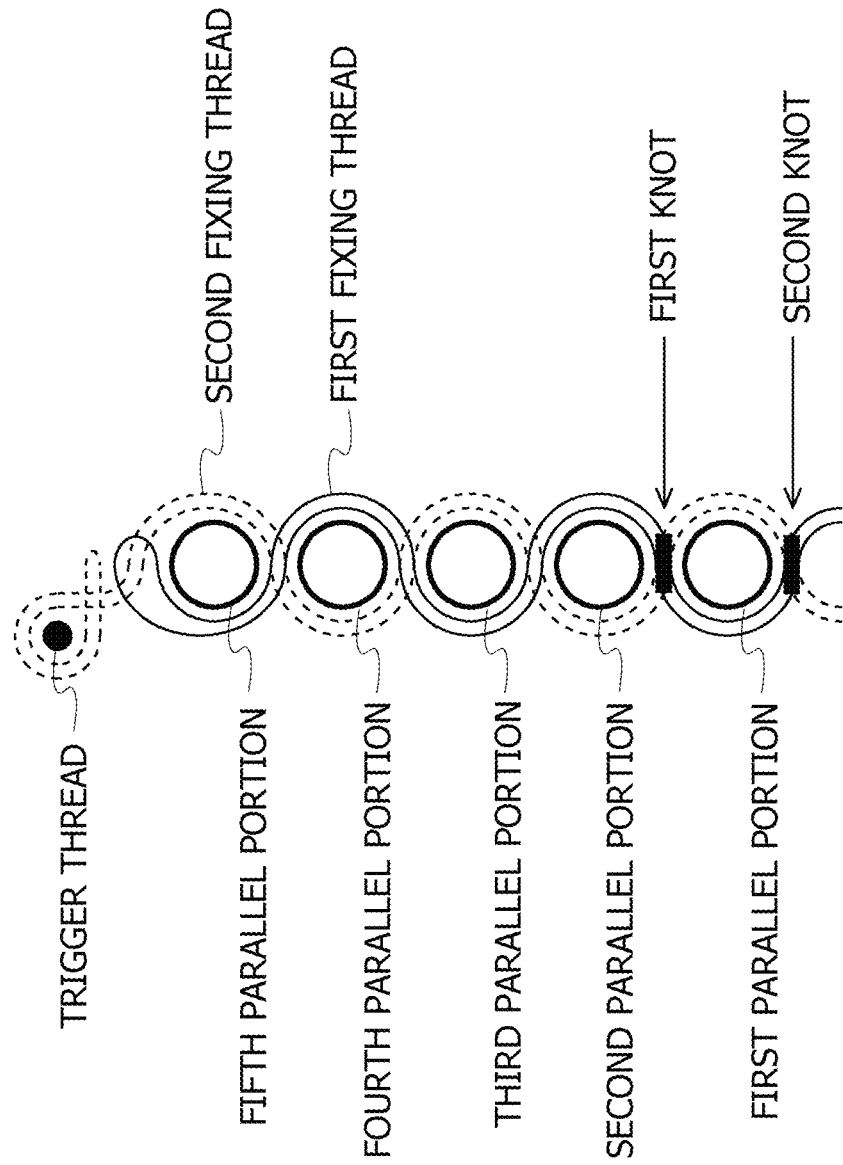
FIG. 13 is an example section view of the middle portion of the tube in the state depicted in FIG. 12.

FIG. 13 is an example section view of the middle portion of the tube in the state depicted in FIG. 12. FIG. 13 illustrates the first fixing thread and the second fixing thread 22 in solid lines and dotted lines, respectively. The first knot is present between the first and second parallel portions, and the second knot is present on the side of the first parallel portion opposite to the first knot.

The spacer 1 is configured as illustrated in FIGS. 12 and 13. The number of folds of the tube 10 and/or the number of fixing threads 20 may be changed as appropriate depending on the size of the spacer 1. A larger number of the second threads 22 may result in greater friction between the trigger thread 30 and the second fixing threads 22 to make it difficult to pull out the trigger thread 30. In this case, the number of trigger threads 30 may be increased. A plurality of trigger threads 30 can overcome the difficulty to pull out the trigger threads 30. Alternatively, to decrease friction between the trigger thread 30 and the second fixing thread 22, how the trigger thread 30 is passed through the second fixing thread 22 may be changed.

Figure 14:
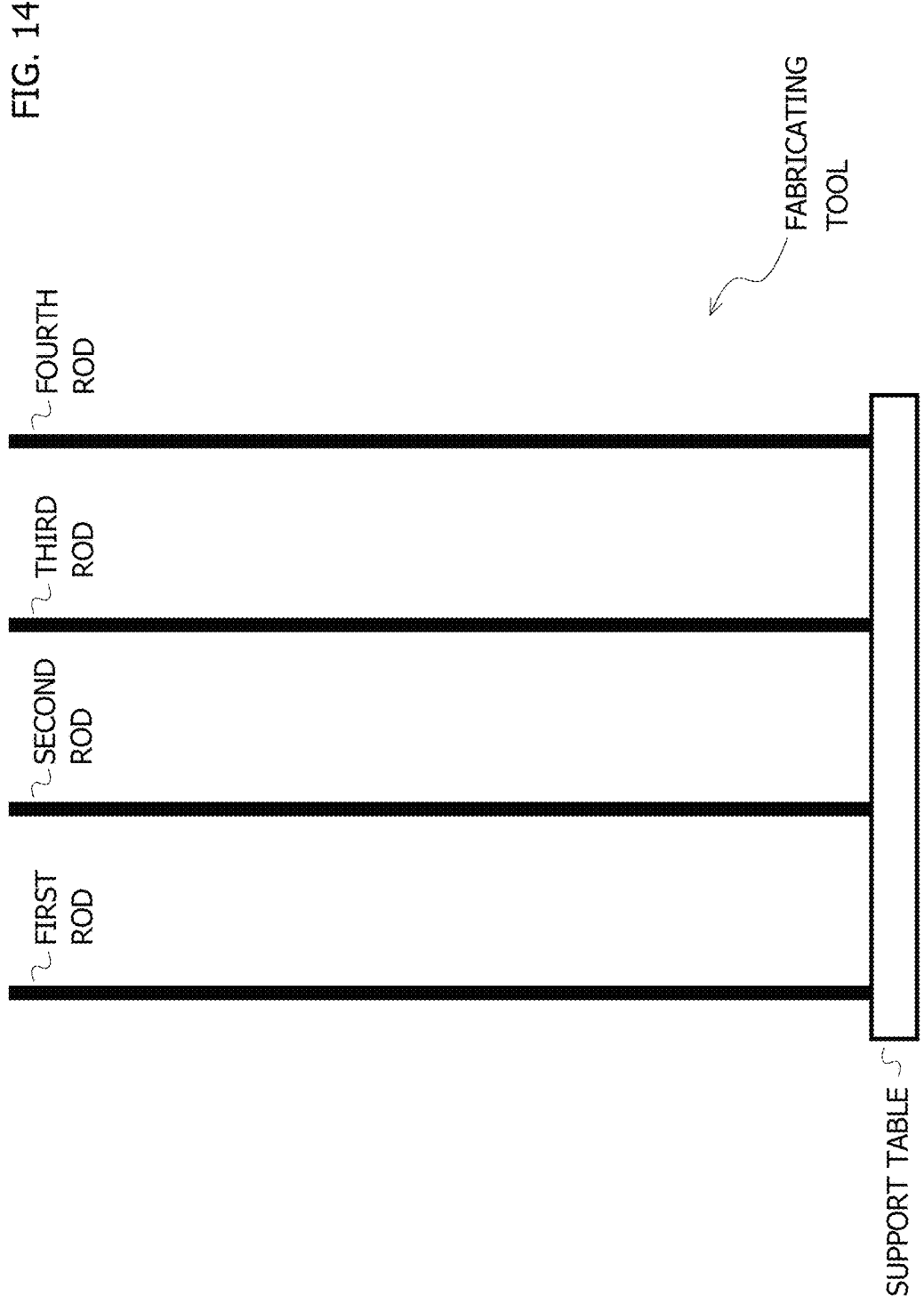
FIG. 14 illustrates an example tool for fabricating the spacer.

FIG. 14 illustrates an example tool for fabricating a spacer. The tool for fabricating a spacer includes a support table and a plurality of rods. The plurality of rods are approximately the same in length. The plurality of rods are evenly spaced in parallel, with one end of each rod secured to the support table. No specific limitation is imposed on how the rods are secured to the support table. For example, a male screw thread may be cut on one end portion of each rod so that the end portion is screwed into a screw hole disposed on the support table. Alternatively, one end portion of each rod may be tapered, i.e., made gradually thinner, to be fit into a hole disposed on the support table. Some supplementary member, e.g., a piece of hardware with an L-shaped cross section, may also be used to secure each rod to the support table. Materials used for the rod may include metals resistant to deformation. The example illustrated in FIG. 14 has four rods, but the number of rods is not limited to four. The individual rods in FIG. 14 are hereinafter called a first rod, a second rod, a third rod, and a fourth rod, from left to right.

Figure 15:
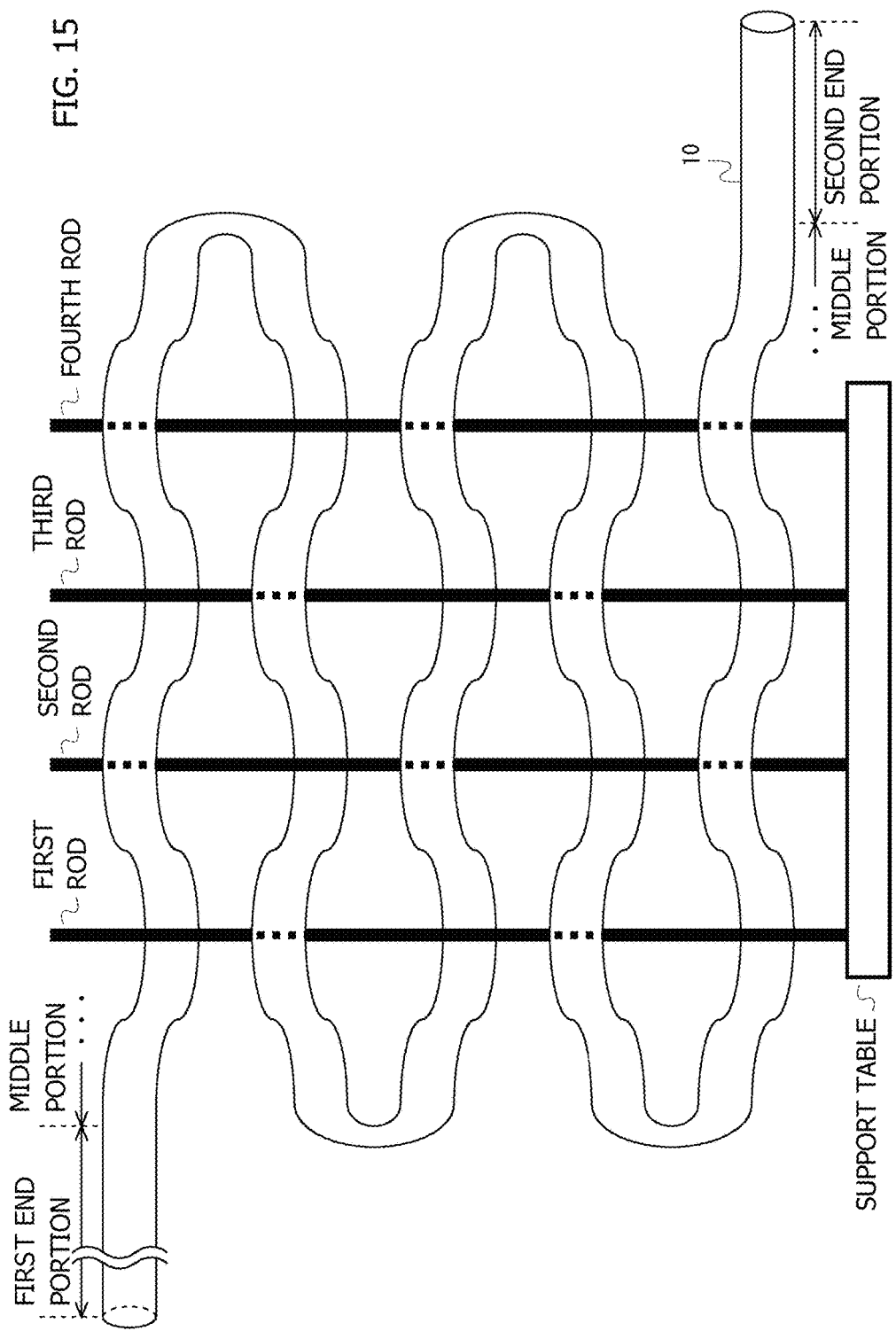
FIG. 15 illustrates an example of using the tool for fabricating the spacer in FIG. 14.

FIG. 15 illustrates an example of using the tool for fabricating the spacer in FIG. 14. The example in FIG. 15 illustrates that the tube 10 is attached on the tool for fabricating the spacer. The tube 10 is running from the first end portion, to the back side of the first rod, to the front side of the second rod, to the back side of the third rod, and to the front side of the fourth rod. Then, the tube 10 is folded, and further running to the back side of the fourth rod, to the front side of the third rod, to the back side of the second rod, and to the front side of the first rod, and then folded again. In this way, the tube 10 is folded a total of four times to be attached to the tool for fabricating the spacer. In FIG. 15, the parts of the rods depicted in dotted lines represent that the tube 10 is running on the front side of the rods where so depicted.

Passing the first fixing thread 21 along the fourth rod from the support table side (the second end portion side) toward the side opposite to the support table achieves the first fixing thread 21 running across the middle portion of the tube 10, as illustrated in FIG. 7. Likewise, passing the second fixing thread 22 along the third rod from the support table side toward the side opposite to the support table achieves the second fixing thread 22 running across the middle portion of the tube 10, as illustrated in FIG. 8. The tool for fabricating the spacer in FIG. 14 allows for passing fixing threads 20 across the tube 10 with ease. After the fixing threads are all passed, pulling out the support table results in the tube 10 and the fixing threads 20 as illustrated in FIG. 8. Alternatively, the tube 10 may remain on the fabricating tool until the fixing threads are passed across the tube, the trigger thread is passed, the first knot is tied, and the second knot is tied, and then the fabricated spacer 1 may finally be removed from the fabricating tool.

In addition, a full-scale design drawing of the spacer to be fabricated can be placed on the back of the rods in the tool for fabricating the spacer. A full-size design drawing placed on the back of the rods in the tool for fabricating the spacer facilitates fabricating the spacer according to the design drawing.

After fabrication, the spacer 1 is preferably subjected to aseptic and sterilizing treatment before embedded in the body. No specific limitation is imposed on the process of aseptic and sterilizing treatment.

Example of Use

Figure 1:
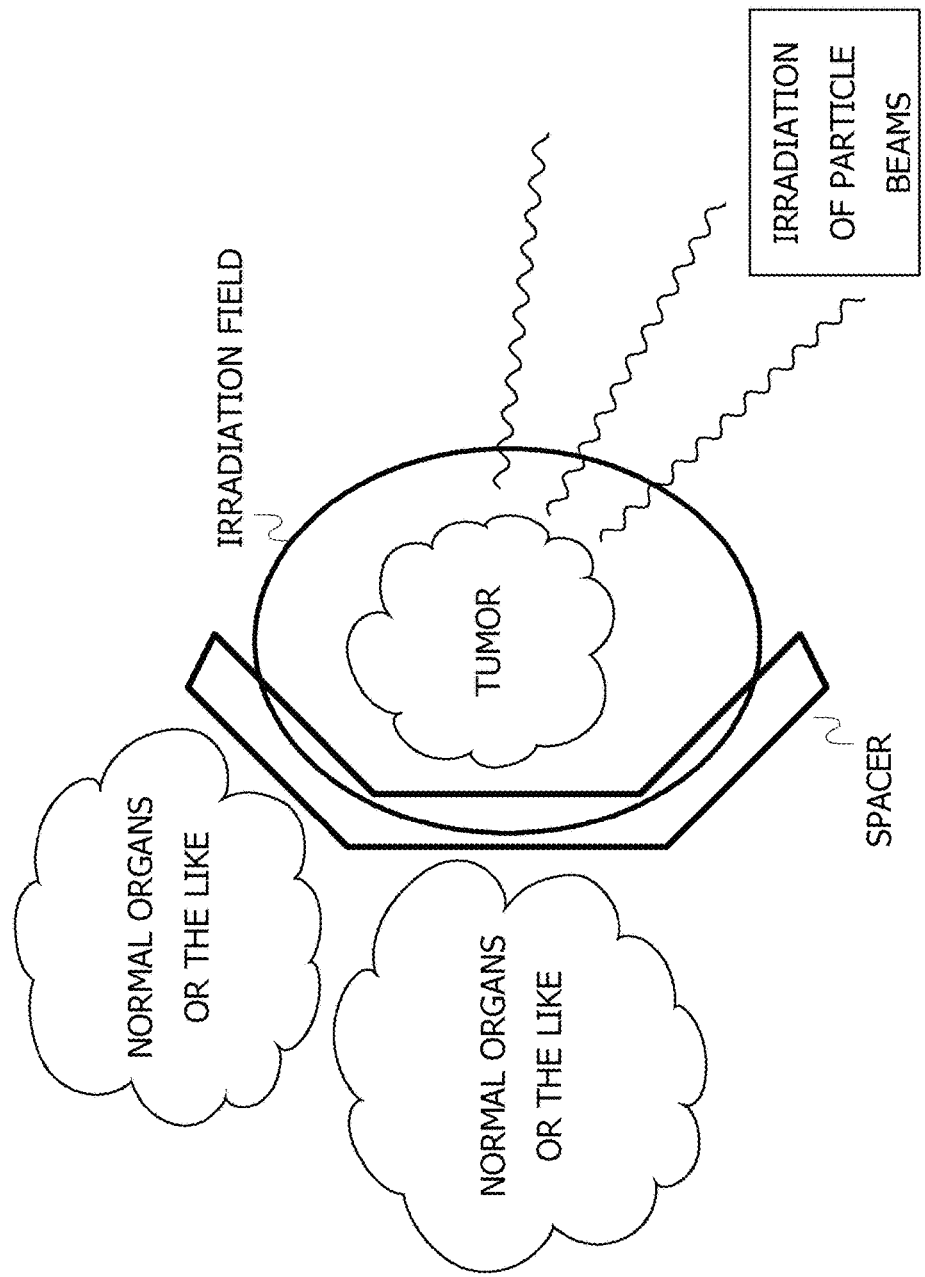

The spacer 1 is embedded through a laparotomy surgery between a tumor and normal organs or the like in the body, as illustrated in FIG. 1. The tumor is the target of irradiation with particle beams or the like. Creating a space with the spacer 1 between the tumor and the normal organs or the like in the body protects the normal organs or the like from being irradiated with particle beams or the like during a particle beam radiation therapy or the like. One end of the tube 10 (the left end of the tube 10 in FIG. 2) in the spacer 1 as well as one end of the trigger thread 30 (the left end of the trigger thread in FIG. 2) are led out of the body and fixed thereon. The tube 10 is led outside the body out of a hole made on the body surface. The tube 10 is led out of the body in a manner similar to a method for leading a drain tube out of the body during a laparotomy surgery. The spacer 1 is fabricated so that its size matches the size of the place where the spacer 1 will be embedded.

Applying a negative pressure on the tube 10 by, for example, connecting a negative-pressure pack to one end of the tube 10 that is led outside the body allows contaminants in the abdominal cavity (e.g., blood, pus, exudate, or digestive fluid) to be aspirated from one end of the tube retained in the body and to be brought to the outside of the body. Infection in the abdominal cavity can be controlled by guiding contaminants from the inside of the abdominal cavity to the outside of the body. Accordingly, when the intestinal tract or the like has an injury, or the intestinal tract or the like has an infection, the spacer 1 can still be embedded in the body. The spacer 1 is particularly suitable for isolating a tumor from the gastrointestinal tract including intestines and the stomach, which are prone to be damaged by irradiation.

The spacer 1 can be used as a spacer for therapies such as heavy particle radiotherapy, radiation therapy, proton beam therapy, and intensity-modulated radiation therapy (IMRT).

After treatment, the spacer 1 is removed out of the body by the following steps. (1) Pull the trigger thread 30 coming out of the body to remove the whole trigger thread 30 from the body. As a result, the second fixing thread 22 is allowed to be released from the trigger thread 30. At the same time, the first fixing thread 21 is also allowed to be easily released from the second fixing thread 22. (2) Pull the tube 10 to remove the whole tube 10 from the body. Because the fixing threads 20 are fastened to the tube 10 with the first and second knots, the fixing threads 20 are also removed along with the tube 10. When the trigger thread 30 is pulled out, the first fixing thread 21 and the second fixing thread 22 are released from the trigger thread 30 side as far as the first knot. Accordingly, individual parallel portions of the tube 10 that have been bound together are now released due to the elasticity of the tube 10, and thus the tube 10 can be removed in the form of one tube. Consequently, the whole spacer 1 is removed out of the body without the need for performing a laparotomy surgery again.

Actions or Effects of Embodiments

The spacer according to the present embodiment can be placed in a surgical field involving infection and can be removed after placement without a laparotomy surgery. The spacer 1 can be created with materials that are usually used inside the abdominal cavity during a surgery, and thus the materials are safe.

The planar portion of the tube 10 in the spacer 1 forms a space between normal organs or the like, such as the intestinal tract, and a tumor, thereby protecting the normal organs or the like, such as the intestinal tract, from being irradiated with particle beams or the like.

Air can be passed between both ends of the tube 10 in the spacer 1, which means infection can be controlled by applying a negative pressure to the tube 10 in the spacer 1 to guide contaminants from the abdominal cavity to the outside of the body, and thus the spacer 1 can be used in a site with an infected wound.

(Variation 1)

Variation 1 of the above-described spacer 1 will now be described. Variation 1 has commonalities with the above-described spacer 1. The following describes differences between Variation 1 and the spacer 1, omitting descriptions of the commonalities.

Figure 16:
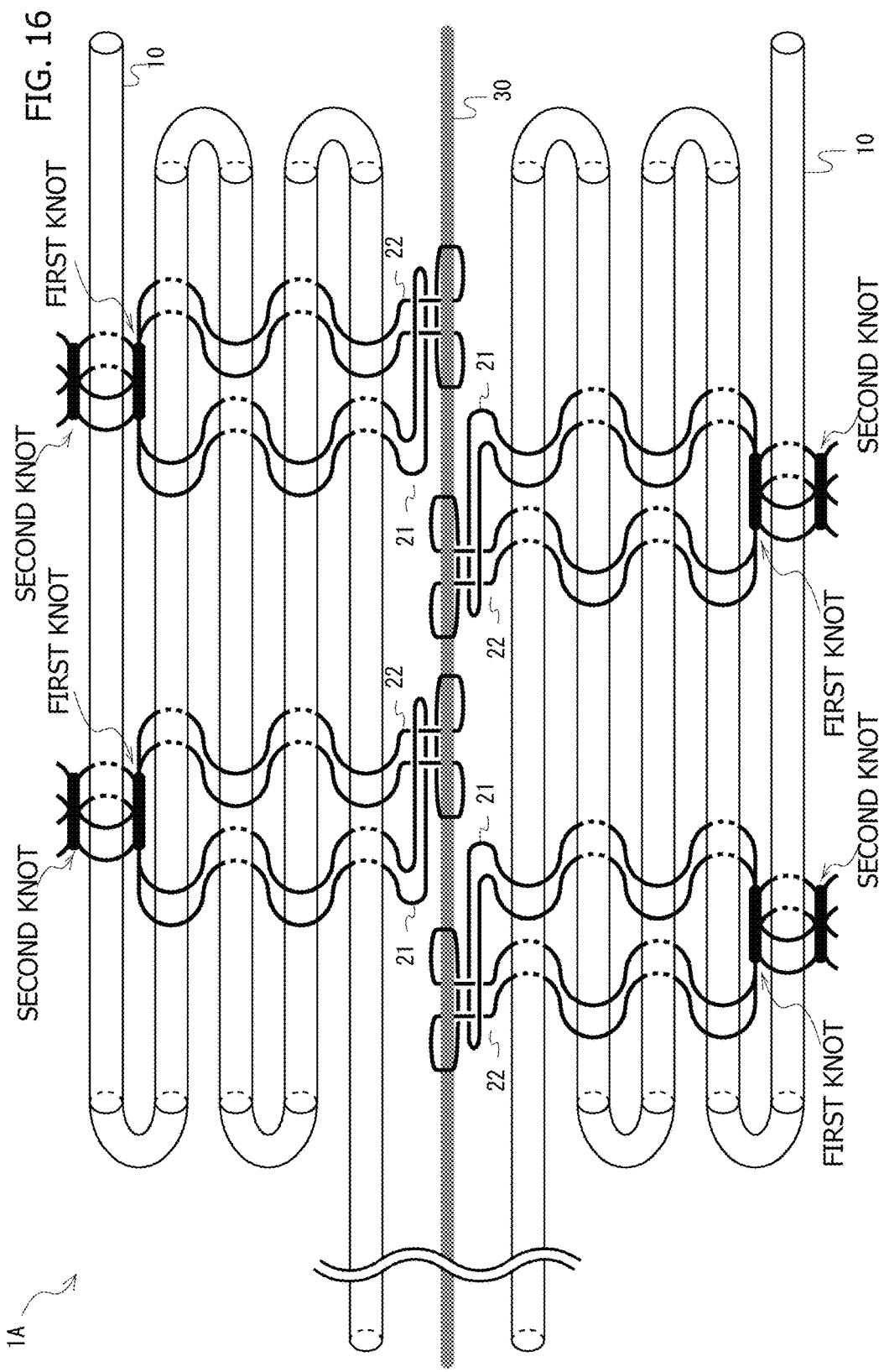
FIG. 16 illustrates an example configuration of the spacer according to Variation 1.

FIG. 16 illustrates an example configuration of a spacer according to Variation 1. The spacer 1A in FIG. 16 includes a tube 10, a first fixing thread 21, a second fixing thread 22, and a trigger thread 30. The pair of one first fixing thread 21 and one second fixing thread 22 may be collectively called fixing threads 20. The spacer 1A in FIG. 16 includes two tubes 10. The spacer 1A in FIG. 16 includes two units of the spacer 1, which is illustrated in FIG. 2, connected to each other with one trigger thread 30. The individual tubes in the spacer 1A are the same as the spacer 1 in shape. That is, each tube 10 includes two end portions and a planar portion formed into a planar shape between the end portions. Similarly to the spacer 1, the fixing threads 20 are fastened to the respective tubes 10 with the first and second knots. The shape of the planar portion in each tube 10 is maintained by the fixing threads 20 that are running along the outer surface of the tubes 10 in such a way that the fixing threads weave between the front side and the back side of the tube 10 in an alternate manner. The example in FIG. 16 illustrates that the spacer 1A includes two pairs of fixing threads 20 for each tube 10; however, the spacer 1A may include two or more pairs of fixing threads 20 for each tube 10. The individual tubes 10 are arranged so that fixing threads 20 for one tube 10 are caught by the trigger thread 30 at a place adjacent to a place where fixing threads 20 for the other tube 10 are caught by the trigger thread 30 and that a second knot for the one tube 10 and a second knot for the other tube are placed away from each other by a greatest distance; consequently, the common trigger thread 30 catches fixing threads 20 for each individual spacer 1. According to the example in FIG. 16, the fixing threads maintaining the shape of each tube 10 are caught by one trigger thread 30. The fixing threads 20 are caught in the same way as described above for the spacer 1. The example in FIG. 16 illustrates that adjacent tubes are spaced apart from each other; however, the actual tubes are formed so that adjacent tubes are in close contact with each other. As a result, the planar portions of the two tubes 10 are put together to form a larger planar portion.

One end of each tube 10 (the left end of each tube 10 in FIG. 16) in the spacer 1A as well as one end of the trigger thread 30 (the left end of the trigger thread 30 in FIG. 16) are led out of the body and fixed thereon. The tube 10 is led outside the body out of a hole made on the body surface.

The example in FIG. 16 illustrates that each fixing thread 20 is passed so as to weave only the outer surface of the tube having knots; however, each fixing thread 20 may additionally be passed so as to weave the outer surface of a tube other than the tube having knots. In this case, the two tubes can be put together more securely.

The spacer 1A uses two tubes 10 to allow for creating a larger spacer. In addition, the spacer 1A uses two tubes 10 to allow contaminants in the abdominal cavity to be drained from two positions in the abdominal cavity to the outside of the body. Furthermore, even when one of the tubes 10 can no longer pass air due to some reason, the spacer 1A is still able to drain contaminants in the abdominal cavity by using the other one of the tubes 10.

(Variation 2)

Variation 2 of the above-described spacer 1 will now be described. Variation 2 has commonalities with the above-described spacer 1. The following describes differences between Variation 2 and the spacer 1, omitting descriptions of the commonalities.

Figure 17:
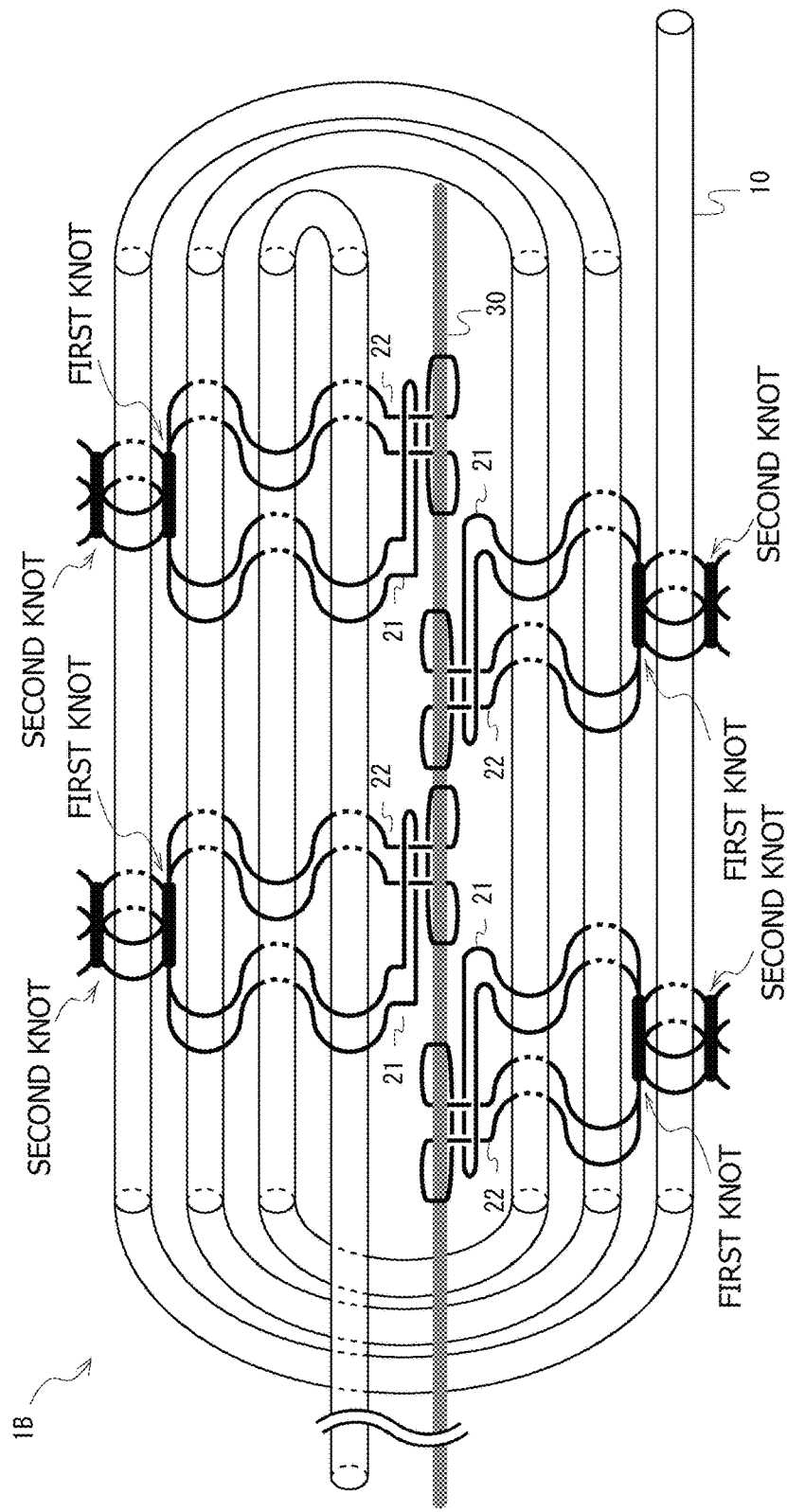
FIG. 17 illustrates an example configuration of the spacer according to Variation 2.

FIG. 17 illustrates an example configuration of a spacer according to Variation 2. The spacer 1B in FIG. 17 includes a tube 10, a first fixing thread 21, a second fixing thread 22, and a trigger thread 30. The tube 10 in the spacer 1B in FIG. 17 includes two end portions and a swirly portion formed into a swirl between the end portions. The swirly portion in the spacer 1B corresponds to the planar portion in the spacer 1. In this way, the spacer 1B may be formed into a swirl by bending and folding the tube 10. In the spacer 1B, the swirly shape of the swirly portion of the tube 10 is maintained by the first fixing thread 21 and the second fixing thread 22. The swirly portion of the tube 10 is formed by winding the tube around a tube section at the center on a substantial plane. Fixing threads 20 are fastened with the first and second knots around the outermost circumference of the swirly portion of the tube 10. The shape of the swirly portion of the tube 10 is maintained by the fixing threads 20 that are running along the outer surface of the tube 10 from the outer perimeter side of the swirly portion to the center, in such a way that the fixing threads weave between the front side and the back side of the swirly tube 10 in an alternate manner. The shape of the swirly portion of the tube 10 is maintained by a plurality of fixing threads 20. The example in FIG. 17 illustrates four pairs of fixing threads 20, but the number of pairs of fixing threads 20 is not limited to four. Each fixing thread 20 is caught by the trigger thread 30. The example in FIG. 17 illustrates adjacent tubes being spaced apart from each other; however, the actual tube is formed so that adjacent tubes are in close contact with each other.

One end portion of the tube 10 in the spacer 1B is extended from the center to the outside of the perimeter of the swirly portion. The trigger thread 30 is placed along the tube 10 extending from the center of the swirly portion. One end portion of the tube 10 (the left end of the tube 10 in FIG. 17) extending from the center of the swirly portion toward the outside is brought out of the body along with one end of the trigger thread 30 (the left end of the trigger thread 30 in FIG. 17). The other end portion of the tube 10 is extended from the perimeter of the swirly portion in the direction tangent to the perimeter. The other end portion of the tube 10 is placed inside the body.

The spacer 1B as configured above allows the tube 10 to be removed beginning from its one end portion located around the center of the swirly portion of the spacer 1B. Selection from the spacer 1, spacer 1A, and spacer 1B to be made depending on the physical condition or the like provides greater flexibility with respect to where to place the spacer or from where to pull out the tube.

The above-described embodiments and variations may be combined to the extent possible. The individual spacers are examples of an implantable spacer.

REFERENCE SIGNS LIST

1 Spacer
10 Tube
20 Fixing thread
21 First fixing thread
22 Second fixing thread
30 Trigger thread
1A Spacer
1B Spacer

The invention claimed is:

1. An implantable spacer comprising:
a tube which is folded or bent at one or a plurality of positions to form partial sections adjacent to each other;
fixing threads which are disposed along a direction transverse to the partial sections to maintain a shape of the tube; and
a trigger thread for catching the fixing threads, wherein the trigger thread is in a releasable state, wherein:
the spacer comprises two sets of the tube, a shape of each tube being maintained by the fixing threads, and each of the fixing threads maintaining the shape of each tube is retained by the trigger thread.

2. The implantable spacer according to claim 1, wherein the fixing threads comprise a first fixing thread and a second fixing thread, and are disposed so that the first fixing thread and the second fixing thread are in contact with an outer surface on opposite sides to each other of each tube in each of the partial sections.

3. The implantable spacer according to claim 2, wherein the first fixing thread and the second fixing thread are respectively disposed, as for a plurality of the partial sections adjacent to each other, on a front side and on a back side in an alternate manner relative to one face of the spacer.

4. The implantable spacer according to claim 1, wherein each tube is folded in such a way that air can be passed between one end of each tube and another end of each tube.

5. The implantable spacer according to claim 1, wherein each tube is formed into a swirly shape.

6. A method for removing an implantable spacer, the method comprising:
embedding in a body an implantable spacer which comprises: a tube which is folded or bent at one or a plurality of positions to form partial sections adjacent to each other; fixing threads which are disposed along a direction transverse to the partial sections in order to maintain a shape of the tube; and a trigger thread for catching the fixing threads, wherein the trigger thread is in a releasable state, wherein one end of the tube and one end of the trigger thread are brought outside the body;
releasing the fixing threads by pulling the one end of the trigger thread to remove the trigger thread out of the body; and
removing the tube and the fixing threads out of the body by pulling the one end of the tube.

7. A method for aspirating contaminants with an implantable spacer, the method comprising:
embedding in a body an implantable spacer which comprises: a tube which is folded or bent at one or a plurality of positions to form partial sections adjacent to each other; fixing threads which are disposed along a direction transverse to the partial sections in order to maintain a shape of the tube; and a trigger thread for catching the fixing threads, wherein the trigger thread is in a releasable state, wherein the tube is folded in such a way that air can be passed between one end of the tube and another end of the tube, and wherein the one end of the tube and one end of the trigger thread are brought outside the body; and
applying a negative pressure to the one end of the tube and aspirating contaminants in the body from the other end of the tube to the outside of the body.

* * * * *

UNITED STATES PATENT AND TRADEMARK OFFICE
CERTIFICATE OF CORRECTION

PATENT NO.           : 10,179,248 B2
APPLICATION NO.  : 15/108352
DATED                    : January 15, 2019
INVENTOR(S)         : Takayuki Asao Page 1 of 1

It is certified that error appears in the above-identified patent and that said Letters Patent is hereby corrected as shown below:

In the Claims

At Column 12, Line 9, "wherein:" should be -- wherein --.

Signed and Sealed this
Eleventh Day of June, 2019

Andrei Iancu
*Director of the United States Patent and Trademark Office*